United States Patent
Son et al.

(10) Patent No.: US 9,880,148 B1
(45) Date of Patent: Jan. 30, 2018

(54) SCALABLE HIGH-DENSITY WIRELESS NEUROELECTRIC SENSOR AND STIMULATOR ARRAY

(71) Applicant: HRL Laboratories, LLC, Malibu, CA (US)

(72) Inventors: Kyung-Ah Son, Moorpark, CA (US); Jeong-Sun Moon, Moorpark, CA (US); Zhiwei A. Xu, Davis, CA (US); Brian N. Limketkai, Santa Monica, CA (US); Jongchan Kang, Moorpark, CA (US); Tahir Hussain, Calabasas, CA (US)

(73) Assignee: HRL Laboratories, LLC, Malibu, CA (US)

(*) Notice: Subject to any disclaimer, the term of this patent is extended or adjusted under 35 U.S.C. 154(b) by 0 days.

(21) Appl. No.: 15/478,129

(22) Filed: Apr. 3, 2017

Related U.S. Application Data

(62) Division of application No. 14/669,794, filed on Mar. 26, 2015, now Pat. No. 9,662,498.

(Continued)

(51) Int. Cl.
*A61N 1/00* (2006.01)
*G01N 33/483* (2006.01)
(Continued)

(52) U.S. Cl.
CPC ......... *G01N 33/4836* (2013.01); *C23C 16/26* (2013.01); *C23C 16/45525* (2013.01);
(Continued)

(58) Field of Classification Search
CPC .... C23C 16/26; C23C 16/45525; C23C 16/56
(Continued)

(56) References Cited

U.S. PATENT DOCUMENTS 9,548,415 B1   1/2017 Son et al.
9,662,498 B1   5/2017 Son et al.
(Continued)

OTHER PUBLICATIONS

Marblestone AH, Zamft BM, Maguire YG, Shapiro MG, Cybulski TR, Glaser JI, Amodei D, Stranges PB, Kalhor R, Dalrymple DA, Seo D, Alon E, Maharbiz MM, Carmena JM, Rabaey JM, Boyden ES, Church GM, and Kording KP "Physical Principles for Scalable Neural Recording", *Frontiers in Computational Neuroscience*, vol. 7, 1, Article 137, Oct. 2013, pp. 1-34.

(Continued)

*Primary Examiner* — Amanda Patton
*Assistant Examiner* — Philip C Edwards
(74) *Attorney, Agent, or Firm* — Ladas & Parry

(57) ABSTRACT

A neuroelectric sensor and stimulator system includes a first antenna, a reader coupled to the first antenna for transmitting stimulation controls and power to a second antenna, and for receiving sensor data transmitted from the second antenna via the first antenna, and at least one neuroelectric sensor stimulator array including the second antenna, a rectifier coupled to the second antenna for extracting power transmitted from the first antenna, a controller coupled to the second antenna for decoding controls transmitted from the first antenna to the second antenna for the neuroelectric sensor stimulator array, a plurality of sensors, a multiplexer coupled to the controller and to the plurality of sensors for selecting a single sensor, and a plurality of stimulators coupled to the controller for stimulating neurons, wherein the rectifier, the controller, the plurality of sensors, the multiplexer, and the plurality of stimulators include graphene.

13 Claims, 10 Drawing Sheets

Related U.S. Application Data

(60) Provisional application No. 61/971,450, filed on Mar. 27, 2014.

(51) Int. Cl.

| | |
|---|---|
| *C23C 16/455* | (2006.01) |
| *C23C 16/56* | (2006.01) |
| *C23C 16/26* | (2006.01) |
| *H01L 21/04* | (2006.01) |
| *H01L 21/02* | (2006.01) |

(52) U.S. Cl.
CPC .......... *C23C 16/56* (2013.01); *H01L 21/0262* (2013.01); *H01L 21/02527* (2013.01); *H01L 21/042* (2013.01); *H01L 21/044* (2013.01)

(58) Field of Classification Search
USPC .......................................................... 607/60
See application file for complete search history.

(56) References Cited

U.S. PATENT DOCUMENTS

| | | |
|---|---|---|
| 2009/0157141 A1 | 6/2009 | Chiao et al. |
| 2013/0338744 A1 | 12/2013 | Frewin et al. |

OTHER PUBLICATIONS

Berényi A, Somogyvari Z, Nagy AJ, Roux L, Long JD, Fujisawa S, Stark E, Leonardo A, Harris TD, and Buzsaki G, "Large-scale, High-Density (up to 512 channels) Recording of Local Circuits in Behaving Animals", *Journal of Neurophysiology* DOI: 10.1152/jn.00785.2013 (2013), pp. 1132-1149.

Frewin CL, Locke C, Mariusso L, Weeber EJ, Saddow SE, "Silicon carbide Neural Implants: In Vivo Neural Tissue Reaction", *Engineering in Medicine and Biology Science*, EMBC 2013, Annual International Conferences of the IEEE, San Diego, CA, Nov. 2013, pp. 661-664.

Abdelhalim K, Jafari HM, Kokarovtseva L, Velazquez JLP, Genov R. "Neural Synchrony-Monitoring Wireless Brain Implant for Intractable Epilepsy Neuromodulation", *Engineering in Medicine and Biology Science*, EMBC 2013, Annual International Conferences of the IEEE, San Diego, CA, Nov. 2013, pp. 65-68.

Agha NS, Komar J, Yin M, Borton DA, and Nurmikko A, "A Fully Wireless Platform for Correlating Behavior and Neural Data from an Implanted, Neural Recording Device: Demonstration in a Freely Moving Swine Model", *Proceedings of Engineering in Medicine and Biology Science*, EMBC 2013, Annual International Conferences of the IEEE, San Diego, CA, Nov. 2013, pp. 989-992.

Borton DA, Yin M, Aceros J, and Nurmikko A, "An Implantable Wireless Neural Interface for Recording Cortical Circuit Dynamics in Moving Primates", *Journal of Neural Engineering*, vol. 10, 026010, (2013), pp. 1-16.

Seo D, Carmena JM, Rabaey JM, Alon E, and Maharbiz MM, "Neural Dust: An Ultrasonic, Low Power Solution for Chronic Brain-Machine Interfaces", arXiv:1307.2196 [q-bio.NC], Jul. 2013, pp. 1-11.

Castagnola E, Maiolo L, Maggiolini E, Minotti A, Marrani M, Maita F, Pecora A, Angotzi GN, Ansaldo A, Fadiga L, Fortunato G, Ricci D, "Ultra-Flexible and Brain-Conformable Micro-Electrocorticography Device with Low Impedance PEDOT-Carbon Nanotube Coated Microelectrodes", Engineering in Medicine and Biology Science, EMBC 2013, Annual International Conferences of the IEEE, San Diego, CA, 2013 p. 927.

Cogan SF, Troyk PR, and DeMichele G, "Stability of Thin-Film Wireless Recording and Stimulation Devices for Epilepsy Monitoring", *Engineering in Medicine and Biology Science*, EMBC 2013, Annual International Conferences of the IEEE, San Diego, CA, Nov. 2013, pp. 1005-1008.

http://www.neuronexustech.com/.

Khodagholy D, Doublet T, Quilichini P, Gurfinkel M, Leleux P, Ghestem A, Ismailova E, Herve T, Sanaur S, Bernard C, & Malliaras GG, "In Vivo Recordings of Brain Activity Using Organic Transistors", Nature Communications 4, 1575 (2013). DOI: 10.1038/ncomms2573., pp. 1-7.

Sarpeshkar R. "Ultra Low Power Bioelectronics" New York, NY: Cambridge University Press. doi: 10.1017/CBO9780511841446 (2010).

U.S. Appl. No. 14/530,365, filed Oct. 31, 2014, Son et al.

Gittis AH, Moghadam SH, and du Lac S "Mechanisms of Sustained High Firing Rates in Two Classes of Vestibular Nucleus Neu- Rons: Differential Contributions of Resurgent Na, Kv3, and BK currents", J. Neurophysiol. 104, pp. 1625-1634, (2010). doi: 10.1152/jn.00378.2010.

Wolf PD, "Thermal Considerations for the Design of an Implanted Cortical Brain-Machine Interface (BMI)," Indwelling Neural Implants: Strategies for Contending with the In Vivo Environment, ed W. M. Reichert (Boca Raton, FL: CRC Press) (2008), Chapter 3, pp. 1-16.

Liu LC, Ho MH, and Wu CY, "A MedRadio-Band Low-Energy Per-Bit CMOS OOK Transceiver for Implantable Medical Devices", *IEEE Biomedical Circuits and Systems Conference*, pp. 153-156, (2011).

Biederman W, Yaeger DJ, Narevsky N, Koralek AC, Carmena JM, Alon E, et al. "A Fully-Integrated, Miniaturized (0.125 mm2 ) 10.5 μW Wireless Neural Sensor", *IEEE J. Solid- State Circuits*, vol. 48, No. 4, Apr. 2013, pp. 960-970.

Myny K, Steudel S, Smout S, Vicca P, Furthner F, van der Putten B, Tripathi AK, Gelinck GH, Genoe J, Dehaene W, and Heremans P, "Organic RFID Transponder Chip With Data Rate Compatible With Electronic Product Coding", *Organic Electronics*, vol. 11, pp. 1176-1179, (2010).

Dagdeviren C, Hwang SW, Su Yewang, Kim S, Cheng H, Gur O, Haney R, Omenetto FG, Huang Y, and Rogers JA, "Transient, Biocompatible Electroncis and Energy Harvesters Based on ZnO", Small, vol. 9, No. 20, pp. 3398-3404, (2013).

Cohen-Karni T, Qing Q, Li Q, Fang Y, and Lieber, CM, "Graphene and Nanowire Transistors for Cellular Interfaces and Electrical Recording", *Nano Letters*. vol. 10, 1098-1102, (2010).

Shen H, Zhang L, Liu M, Zhang Z, "Biomedical Applications of Graphene", *Theranostics* 2(3), 283-294, (2012).

Shao Y, Wang J, Wu H, Liu J, Aksay IA, Lina Y, "Graphene Based Electrochemical Sensors and Biosensors: A Review", *Electroanalysis* 2010, 22, No. 10, pp. 1027-1036.

Bendali A, Hess LH, Seifert M, Forster V, Stephan A-F, Garrido JA, and Picaud S, "Purified Neurons Can Survive on Peptide-Free Graphene Layers", *Advanced Healthcare Materials* 2, 929 (2013).

Hess LH, Seifert M, Garrido JA, "Graphene Transistors for Bioelectronics", *Proceedings of the IEEE*, vol. 101, No. 7, 1780-1792, Jul. 2013.

Moon JS, Seo HC, Stratan F, Antcliffe M, Schmitz A, Ross RS, Kiselev AA, Wheeler VD, Nyakiti LO, Gaskill DK, Lee KM, and Asbeck PM, "Lateral Graphene Heterostrucure FETs", IEEE Electron Device Letters, vol. 34, No. 9, 1190-1192, Sep. 2013.

Moon JS, Curtis D, Bui S, Hu M, Gaskill DK, Tedesco JL, Asbeck P, Jernigan GG, VanMil BL, Myers-ward RL, Eddy CR Jr., Campbell PM, and Weng X, "Top-Gated Epitaxial Graphene FETs on Si-Face SiC Wafer With a Peak Transconductance of 600 mS/mm", *IEEE Electron Device Letters*, vol. 31, No. 4, pp. 260-262, Apr. 2010.

Moon JS, "Advances in Graphene RF Electronics" (Invited), Proceedings of International Microwave Symposium (2013).

Moon JS, Antcliffe M, Seo HC, Curtis D, Lin S, Schmitz A, Milosavljevic M, Kiselev AA, Ross RS, Gaskill DK, Campbell PM, Fitch RC, Lee KM, and Asbeck P, "Ultra-Low Ohmic Contacts to Graphene FETs", *Applied Physics Letters*, 100, 203512-1-203512-3 (2012).

Moon JS, Curtis D, Zehnder D, Kim S, Gaskill DK, Jernigan GG, Myers-ward RL, Eddy CR Jr., Campbell PM, Lee KM, and Asbeck P, "Low-Phase-Noise Graphene FETs in Ambipolar RF Applications", *IEEE Electron Device Letters*, vol. 32, No. 3, pp. 270-272, Mar. 2011.

(56) References Cited

OTHER PUBLICATIONS

Chen P, Cho SY, and Jin H-J, "Modification and Applications of Bacterial Celluloses in Polymer Science", *Macromolecular Research*, vol. 18, No. 4, pp. 309-320 (2010). DOI 10.1007/s13233-010-0404-5.

Kim Y, Jung R, Kim H-S, Jin H-J, "Transparent Nanocomposites Prepared by Incorporating Microbial Nanofibrils Into Poly(L-lactic acid)", Current Applied Physics,9, S69-S71, (2009).

Park W-I, Kim H-S, Kwon S-M, Hong Y-H, Jin H-J, "Synthesis of Bacterial Celluloses in Multiwalled Carbon Nanotube-Dispersed Medium", *Carbohydrate Polymers*, vol. 77,pp. 457-463, (2009).

Jung R, Kim Y, Kim H-S, and Jin H-J, "Antimicrobial Properties of Hydrated Cellulose Membranes With Silver Nanoparticles", Journal of Biomaterials Science, vol. 20, pp. 311-324 (2009).

Jung R, Kim H-S, Kim Y, Kwon S-M, Lee HS, Jin H-J, "Electrically Conductive Transparent Papers Using Multiwalled Carbon NanotubeS", *Journal of Polymer Science: Part B: Polymer Physics*, vol. 46, pp. 1235-1242, (2008).

Fu Lina, Zhang Yue, Zhang Jin and Yang Guang, "Bacterial Cellulose for Skin Repair Materials", Chapter 13 of Biomedical Engineering—Frontiers and Challenges, book edited by Reza Fazel-Rezai, pp. 249-275, (2011), ISBN 978-953-307-309-5. DOI: 10.5772/24323.

Dugan JM, Gough JE, Eichhorn SJ, "Bacterial Cellulose Scaffolds and Cellulose Nanowhiskers for Tissue Engineering", Nanomedicine 8, 297 (2013).

Fernando G. Torres, Solene Commeaux, and Omar P. Troncoso, "Biocompatibility of Bacterial Cellulose Based Biomaterials", J. Funct. Biomater, 2012, 3, 864-878, (2012). doi:10.3390/jfb3040864.

Czaja WK, Young DJ, Kawecki M, and R. Malcolm Brown RM, Jr., "The Future Prospects of Microbial Cellulose in Biomedical Applications", Biomacromolecules, vol. 8, No. 1, pp. 1-12, (2007).

Kang YJ, Chun S-J, Lee S-S, Kim B-Y, Kim JH, Chung H, Lee S-Y, and Kim W, "All-Solid-State Flexible Supercapacitors Fabricated with Bacterial Nanocellulose Papers, Carbon Nanotubes, and Triblock-Copolymer Ion Gels", ACS Nano, vol. 6, No. 7, 6400-6406, (2012).

Pereira AT, Ferreira Q, Freire CSR, Fernandes SCM, Trovatti E, Neto CP, Silvestre AJD, Morgado J, Luís Alcácer L, "Bacterial Cellulose as Substrate for Inkjet Printing of Organic Thin Film Transistors", ICOE 2012 Abstract.

Legnani C, Vilani C, Calil VL, Barud HS, Quirino WG, Achete CA, Ribeiro SJL, Cremona M, "Bacterial Cellulose Membrane as Flexible Substrate for Organic Light Emitting Devices", Thin Solid Films 517, pp. 1016-1020, (2008).

Alcacer L, Morgado J, Ferreira Q, Pecoraro E, Neto CP, Silvestre AJD, Freire CSR, Trovatti E, Fernandes SCM, "Biocellulose Based Materials for Organic Field Effect Transistors" Proc EUROCON and CONFTELE 2011, Lisbon, Portugal, Apr. 2011.

Gaspar D, Fernandes SN, Oliveira AG de, Fernandes JG, Grey P, Pontes RV, Pereira L, Martins R, Godinho MH and Fortunato E, "Nanocrystalline Cellulose Applied Simultaneously as the Gate Dielectric and the Substrate in Flexible Field Effect Transistors", Nanotechnology 25 094008 (2014). doi:10.1088/0957-4484/25/9/094008, 11pgs.

Shah J, Brown RM Jr., "Towards Electronic Paper Displays Made From Microbial Cellulose", Appl Microbial Biotechnol 66, pp. 352-355, (2005). DOI 101007/s00253-004-1756-6.

Sawan M., Mounaim F, Lesbros G, "Wireless Monitoring of Electrode Tissues Interfaces for Long Term Characterization," Analog Integrated Circuits Signal Processing 55, pp. 103-114, (2008).

Chen WM, Chiueh H, Chen TJ, Ho CL, Jeng C, Ker MD, Lin CY, Huang YC, Chou CW, Fan TY, Cheng MS, Hsin YL, Liang SF, Wang YL, Shaw FZ, Huang YH, Yang CH, Wu CY, "A fully Integrated 8-Channel Closed Loop Neural Prosthetic CMOS Soc for Real-Time Epileptic Seizure Control", IEEE Journal of Solid-State Circuits, vol. 49, No. 1, pp. 232-247, Jan. 2014.

Moon JS, Seo HC, Son KA, Yang B, Wong D, Le D, McGuire C, "20 Mb/s Zero-Power Graphene-On-Glass Microwave Envelope Detectors for Ubiquitous Ultra-Low-Power Wireless Network," in press, 2014 IEEE IMS.

Tucker RS, Hinton K, "Energy Consumption and Energy Density in Optical and Electronic Signal Processing," IEEE Photonics Journal, vol. 3, No. 5, pp. 821-833, (2011).

Baker M and Sarpeshkar R, "Feedback Analysis and Design of RF Power Links for Low-Power Bionic Systems", IEEE Trans. Biomedical Circuits and Systems, vol. 1, No. 1, pp. 28-38, Mar. 2007.

Ekanadham C., Tranchina D., Simoncelli EP. A blind Deconvolution Method for Neural Spike Identification, Neural Information Processing Systems. 2011.

From U.S. Appl. No. 14/669,794 (Now U.S. Pat. No. 9,662,498) Restriction Requirement dated Aug. 15, 2016.

From U.S. Appl. No. 14/669,794 (Now U.S. Pat. No. 9,662,498) Non Final Office Action dated Sep. 15, 2016.

From U.S. Appl. No. 14/669,794 (Now U.S. Pat. No. 9,662,498) Notice of Allowance dated Jan. 27, 2017.

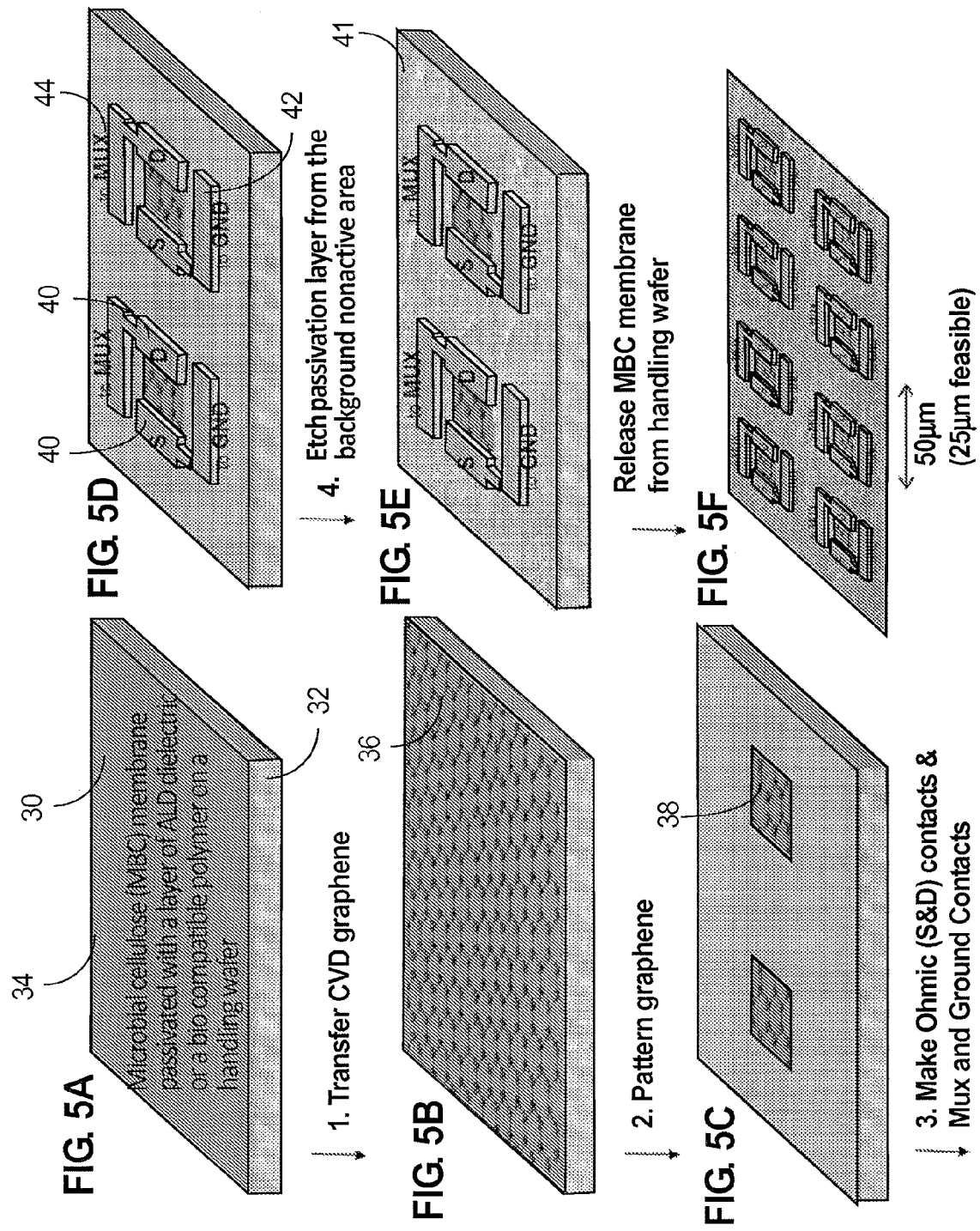

FIG. 6C
FIG. 6B
FIG. 6A
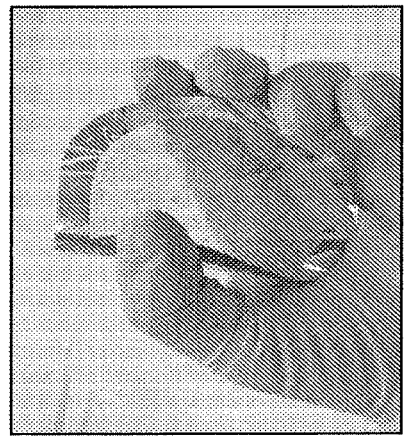
FIG. 6D

SCALABLE HIGH-DENSITY WIRELESS NEUROELECTRIC SENSOR AND STIMULATOR ARRAY

CROSS REFERENCE TO RELATED APPLICATIONS

This application claims the benefit of and is a divisional of U.S. patent application Ser. No. 14/669,794 filed on Mar. 26, 2015, which relates to and claims the benefit of priority from U.S. Provisional Patent Application No. 61/971,450, filed on Mar. 27, 2014, the disclosures of which are hereby incorporated herein by reference in their entireties.

STATEMENT REGARDING FEDERAL FUNDING

None

TECHNICAL FIELD

This disclosure relates to neuroelectric sensors and stimulators for stimulating and monitoring brain activity.

BACKGROUND

Neural circuits incorporate functional activity over a wide range of spatial and temporal scales. Groups of neurons associated with any given task or cognitive operation are typically distributed over different areas. To investigate brain mechanisms related to a specific behavior or cognitive process, it is essential to monitor neuronal activities over various regions of the brain at multiple time scales. In the prior art, microelectrode arrays (MEAs) are widely used to measure neural activities because of their high temporal resolution and their accessibility to various structures of the brain. However, MEAs have significant limitations in scalability and are not ideal for simultaneous high-density, large-area recording at the resolution of single neurons.

Microelectrode arrays (MEAs) detect neuron spikes and measure the local field potential (LFP) generated and are commonly used to monitor neural brain activities because of the high temporal resolution (<1 ms) they provide. However, the large number of monitoring sites required for whole brain recording presents significant challenges in implementing MEA-based systems, such as in vivo integration, power requirements, energy dissipation, and signal transmission and processing. For example, recording spikes of all neurons in a mouse brain using prior art MEA metal electrodes would require ~7.5×10$^6$ sensing electrodes, assuming a signal-to-noise-ratio (SNR) of <100 and a maximum recording distance ($r_{max}$) of 130 μm, as described in Reference 1 below. Reference 1 and References 2-49 are listed below and are incorporated by reference.

One of the largest scale MEAs reported to date consists of eight silicon (Si) neural probes (shanks) fabricated with 32 electrodes on each Si probe, totaling 256 signal channels, as described in Reference 2 below. While the Si probes provide access to deep brain layers, enabling investigation of interactions of multiple brain regions, the Si probes are invasive and induce inflammatory responses from glial cells, as described in Reference 3 below. In addition, the inter-probe distance of 300 μm and the inter-electrode distance of 50 μm on each Si probe reported for the 256-channel MEA are not an optimal solution for spike sorting, necessitating higher density, larger scale electrode arrays. Furthermore, the extracranial headstage for MEA backend electronics is large—the printed circuit is 3.4 cm×3.9 cm×2.5 mm, heavy and connected with long wires to the main control electronics, which is not ideal for studying neural activities of freely moving small rodents.

A wireless implantable system-on-a-chip for neural recording and stimulation has been demonstrated with 64 neural recording channels and 64 neural stimulation channels, and used for validating epilepsy treatment, as described in Reference 4 below. Built with standard CMOS technology, the 12 mm$^2$ system-on-a-chip is not biocompatible and is reported to have dissipation power of 1.4 mW for recording and 1.5 mW for stimulation, which limits its scalability for in vivo applications. A wireless, implantable platform for neural activity monitoring has been reported with a 100-element silicon-based MEA, as described in References 5 and 6 below. The reported dissipation power of the wireless platform is 100 mW, and the platform is powered with a Li battery, which requires recharging every eight hours and requires liquid cooling. This results in the implantable wireless platform not being scalable and not being suitable for large-area brain recording.

A proof-of-concept demonstration for embeddable Neural Dust has also been reported, as described in Reference 7 below. Scaling neural dust to useful quantities is not realistic: deployment via the capillary network becomes unrealistic and analysis of many free-floating data sources would be very challenging.

While the neural activity monitoring systems mentioned above are fabricated on rigid surfaces, MEAs fabricated on flexible polymer substrates, such as polyimide, polydimethylsiloxane (PDMS), and parylene, have also been explored for neural activity recording and stimulation devices, as described in References 8, 9 and 10 below. MEAs consisting of a 4×8 electrode array and made of poly(3,4-ethylenedioxythiophene) (PEDOT)-carbon nanotube (CNT)-coated microelectrodes (200×200 μm size, 400 μm pitch) have been used to measure the local field potentials (LFPs) of the rat somatosensory cortex, as described in Reference 8 below. The scaling limitations of PEDOT-CNT-coated MEAs is similar to those of conventional metal-based MEAs. Due to their ultra-flexible nature, PEDOT-CNT MEAs are optimal for recording neural activities from the cortex surface, but has limited applicability for depth probing.

Table 1 compares prior art brain neural sensors, including an organic electrochemical transistor (OECT) sensor, as described in Reference 11 below, and shows the key challenges of brain monitoring. The prior art sensors can support the required signal to noise ratio (SNR); however, the prior art sensors have a direct current (DC) power consumption that is well over a brain limit of 40 mW/cm$^2$, which is a limit set so to not raise a local brain temperature and disturb neural activities.

TABLE 1

NEUROELECTRIC SENSOR COMPARISON OF PRIOR ART TO PRESENT DISCLOSURE VERSUS BRAIN CONSTRAINT

| Brain Sensor Specification | Brain Constraint[1] | Graphene sensor of the present invention | Organic Transistor sensor | Metal electrodes |
|---|---|---|---|---|
| Dimension (μm$^2$) | 50 × 50 | <20 × 20 | <20 × 20 | |
| Max. Power consumption (μW) | 1 | ~1 | ~80 | |
| Signal to Noise ratio (1 mV spike) | — | ~30 dB | 32 dB | 13 dB |

TABLE 1-continued

NEUROELECTRIC SENSOR COMPARISON OF PRIOR
ART TO PRESENT DISCLOSURE VERSUS BRAIN CONSTRAINT

| Brain Sensor Specification | Brain Constraint[1] | Graphene sensor of the present invention | Organic Transistor sensor | Metal electrodes |
|---|---|---|---|---|
| Noise floor (@ 10 kHz reading) | — | <30 nA | 21 nA | 2.1 mV |
| Speed | ~1 KHz | ~GHz | ~1 kHz | |
| Wireless (high data rate) | — | Yes | No | No |
| Flexibility, Bio-compatibility | desired | Yes, Yes | Yes , Yes | No, Yes |

[1]Total power dissipation of 40 mW/cm$^2$ is used so not to raise the local brain temperature and disturb neural activities.

Brain monitoring electronics empowered with high-spatiotemporal electrical recording of neural activity offers a transformative capability to understanding the brain and possible cures for degenerative brain diseases. Action potentials (spikes) have average durations of =2 msec with an average repetition rate of 0.5 Hz-1 kHz, as described in References 12 and 13 below. With human brain neuron densities of $8 \times 10^{10}/1200$ cm$^3$, the total data rate from a human brain is about 800 Tbits/sec or 670 Gbits/sec/cm$^3$ with a 10 kHz sampling rate, which oversamples neural signals to enable sorting of neural spikes.

Although the required data rate for the high-density sensor is at least 100× lower than existing modern short-range wireless links, for example, 1 Mbit/sec for the 2.4 GHz low-power Bluetooth IEEE 802.15.1 standard, brain interfacing radio frequency (RF) electronics and wireless links have yet to be developed. Key challenges include: (1) meeting an ultra-low-power budget that is scalable to a whole brain interfacing capability, (2) low bit error and high data rate communication, (3) long-term power management, (4) small chip size to prevent damage to the brain, and (5) flexible and biocompatible with congruent contact to the corrugated brain surfaces, as shown in the brain constraints of Table 2.

In order not to disturb neural activities, the maximum allowed local temperature increase is ~2° C., which limits heat dissipation to ~40 mW/cm$^2$, as discussed in reference to Table 1, and further described in Reference 14 below. This sets the total power budget of the sensor wireless electronics. Given a power budget to monitor an area of 50×50 μm$^2$ with ~8 neurons of 1 μW, the transmission energy through a neural wireless link is limited to 12 pJ/bit.

Prior art silicon CMOS transceivers for implantable medical applications have shown 2 Mb/sec On-Off-Key (OOK) communications, but with an excessive total power consumption of 1430 μW and energy per bit of 295 pJ/bit for the receiver, as described in Reference 15 below. Even with the adoption of new envelope demodulator circuits, the overall power dissipation and energy-per-bit is too high, way above the ~40 mW/cm$^2$ limit. Leveraging advanced CMOS technologies, successive approximation register analog to digital converters (ADCs), as described in Reference 4 below, have also been used with sophisticated digital signal processors to deconstruct neuron signals into amplitude and phase data, and with digital filters to process the detected neuron activities. This approach greatly reduces the data communication bandwidth and simplifies the external reader requirement. However, even with a relatively low processing rate, 64 channels of neuron recording still dissipate ~1.4 mW Wirelessly powered radio frequency Identification (RFID) architectures can offer very low energy per bit with ultra-low power operation. Wireless neural sensors have been demonstrated using 65 nm CMOS technology with power consumption as low as 2.6 μW/channel at a 1 Mbit/sec data rate, as described in Reference 16 below. However, the demonstrated wireless neural sensor is invasive and limited in scaling as it uses Si shanks, and also its total required RF power is ~50 mW.

Another key requirement of the wireless electronics is flexibility and bio-compatibility, which is highly desirable for long-term monitoring of freely-moving animals, eventually including humans. A bio-compatible and flexible implantable RFID was demonstrated using organic (penta-

TABLE 2

Wireless specifications for brain neural activity recording compared to present disclosure and prior art.

| Brain interfacing Wireless link Specification | Brain Constraint[1] | Innovations & Comparison to SOA | | Pentacene FETS | 65 nm CMOS RFID | 180 nm CMOS |
|---|---|---|---|---|---|---|
| | | GHz graphene of the present invention | | | | |
| Wireless architecture | | RFID | High-speed sensing[2] | RFID | RFID | Transceiver |
| Sampling rate (kHz) per sensor | 10 | 10 | 1000 | 10 | 10 | 10 |
| Max. Multiplexing ratio | | 1000:1 | 10:1 | 5:1 | 100:1 | 200:1 |
| Data rate needed | 83 kb/s | 10 Mb/s | 10 Mb/s | 50 kb/s | 1 Mb/s | 2 Mb/s |
| RF link area (mm$^2$) | | 1 × 1 for 1000 sensors | | | 0.25× 0.45 | 0.71× 0.78 |
| Max. Power consumption (μW) | 1 | ~1 | | | 2.6 | 1430 |
| Max. Energy per bit (pJ/bit) | 12 | <1 | | | 2.6 | 295 |
| Flexibility, Bio-compatibility | desired | Yes, Yes | | Yes, ? | No, No | No, No |

1) Total RF power dissipation of 10 mW/cm$^2$ is used so not to raise the local brain temperature and disturb neural activities.
2) The high-speed sensing will be carried out in case of stimulating a sub-group of sensors for higher temporal resolution (0.1 μsec) along the axon.

cene) transistors, as described in Reference 17 below. Its frequency was limited to 13.56 MHz with a low data rate of 53 kb/sec. A large supply voltage of 18 Volts was needed due to the poor electronic mobility of 0.5 $cm^2/Vs$ and the low driving current of the organic transistors. Other bio-compatible and flexible devices such as ZnO thin film transistors (TFTs) also showed very poor electronic mobility of 0.95 $cm^2/Vs$, as described in Reference 18 below.

What is needed is simultaneous recording of the single cell activity of large numbers of neurons over various regions of the brain with high spatial resolution. Also needed is a capability to simultaneously stimulate the neurons and record neural activity by individual electrodes/sensors on the array in order to understand the functional relationships between neurons. The embodiments of the present disclosure address these and other needs.

SUMMARY

In a first embodiment disclosed herein, a neuroelectric sensor and stimulator system comprises a first antenna, a reader coupled to the first antenna for transmitting stimulation controls and power to a second antenna, and for receiving sensor data transmitted from the second antenna via the first antenna, and at least one neuroelectric sensor stimulator array comprising the second antenna, a rectifier coupled to the second antenna for extracting power transmitted from the first antenna to the second antenna for the neuroelectric sensor stimulator array, a controller coupled to the second antenna for decoding controls transmitted from the first antenna to the second antenna for the neuroelectric sensor stimulator array, a plurality of sensors, a multiplexer coupled to the controller and to the plurality of sensors for selecting a single sensor, and a plurality of stimulators coupled to the controller for stimulating neurons, wherein the rectifier, the controller, the plurality of sensors, the multiplexer, and the plurality of stimulators comprise graphene.

In another embodiment disclosed herein, a method of providing a neuroelectric sensor and stimulator array comprises providing an antenna, providing a rectifier coupled to the antenna for extracting power received by the antenna, providing a controller coupled to the antenna for decoding controls received by the antenna, providing a plurality of sensors, providing a multiplexer coupled to the controller and to the plurality of sensors for selecting a single sensor, and providing a plurality of stimulators coupled to the controller for stimulating neurons, wherein the rectifier, the controller, the plurality of sensors, the multiplexer, and the plurality of stimulators comprise graphene.

In yet another embodiment disclosed herein, a method for fabricating a graphene-based neuroelectric sensor comprises providing a bio-compatible microbial cellulose (MBC) membrane on a handling wafer, passivating the bio-compatible microbial cellulose (MBC) membrane with an atomic layer deposition (ALD) of dielectric or with a bio-compatible polymer, transferring chemical vapor deposition (CVD) grown graphene over the passivated bio-compatible microbial cellulose (MBC) membrane, patterning the transferred CVD grown graphene, etching the patterning CVD grown graphene to form a graphene mesa structure, forming ohmic contacts on the graphene mesa structure for source and drain electrodes, and releasing the bio-compatible microbial cellulose (MBC) membrane from the handling wafer These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

FIGS. 5A, 5B, 5C, 5D, 5E and 5F show a fabrication process for a GFET-based neuroelectric sensor on microbial cellulose membrane in accordance with the present disclosure;

FIG. 6A shows a SEM image of CVD graphene transferred over a silver nanowire network, FIG. 6B shows a SEM image of CVD graphene transferred over a passivated MBC film, FIG. 6C shows a SEM image of CVD graphene transferred over a 1-μm-high metal contact, and FIG. 6D shows a photograph of graphene active devices fabricated on a PET substrate in accordance with the present disclosure;

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figure 1:
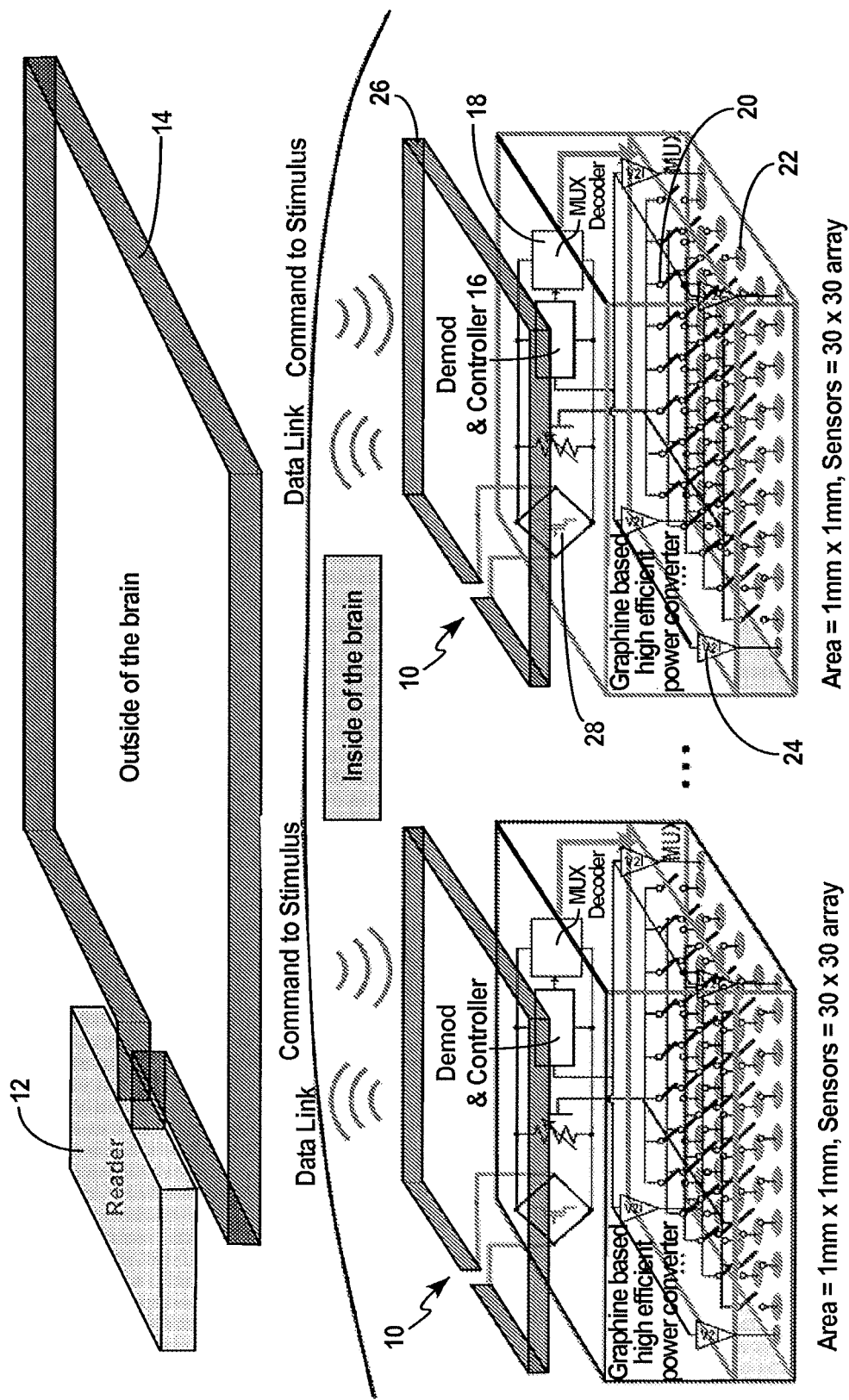
FIG. 1 shows a scalable wireless neuroelectric sensor and stimulator arrays system (WINSS) in accordance with the present disclosure.

The present disclosure is for a scalable WIreless Neuroelectric Sensor and Stimulator Array System (hereinafter referred to as WINSS), shown in FIG. 1, that enables simultaneous high-density, large-scale, for example ~3 k×3 k, recording of neuronal firing and local field potentials over several regions of the brain and localized stimulation of neural circuits in vivo. Outside the brain, the WINSS has a reader 12 and an antenna 14, which can be a coil, as shown in FIG. 1. The reader 12 and the antenna 14 together may sometimes be referred to collectively as the reader. Inside the brain the WINSS includes multiple sensor stimulator arrays 10, each of which include demodulator and control 16, a MUX decoder 18, a multiplexer 20, graphene-based neuroelectric sensors 22, neuron stimulators 24, antenna 26 and a wireless energy harvesting device 28, which as described below may be a direct current (DC) rectifier. The sensor stimulator arrays 10 may be referred to as probes. The antenna 14 and the antenna 26 provide a wireless communication link between the inside and outside of the brain for both sensor data, stimulation controls, and power. The reader 12 includes a transmitter for sending stimulation controls and power to the antenna 26 inside the brain, and a receiver for receiving sensor data via the antenna 26 inside the brain. The WINSS uses graphene electronic devices to take advantage of their high mobility, low 1/f noise, high cut-off frequency, low power dissipation, biocompatibility, and flexibility. The WINSS may be fabricated on microbial cellulose (MBC) membranes for biocompatibility, bio-permeability, and ultra-flexibility. The WINSS overcomes the limitations of prior art neuroelectric sensors and provides transformative capabilities in brain recording and stimulation.

Figure 2:
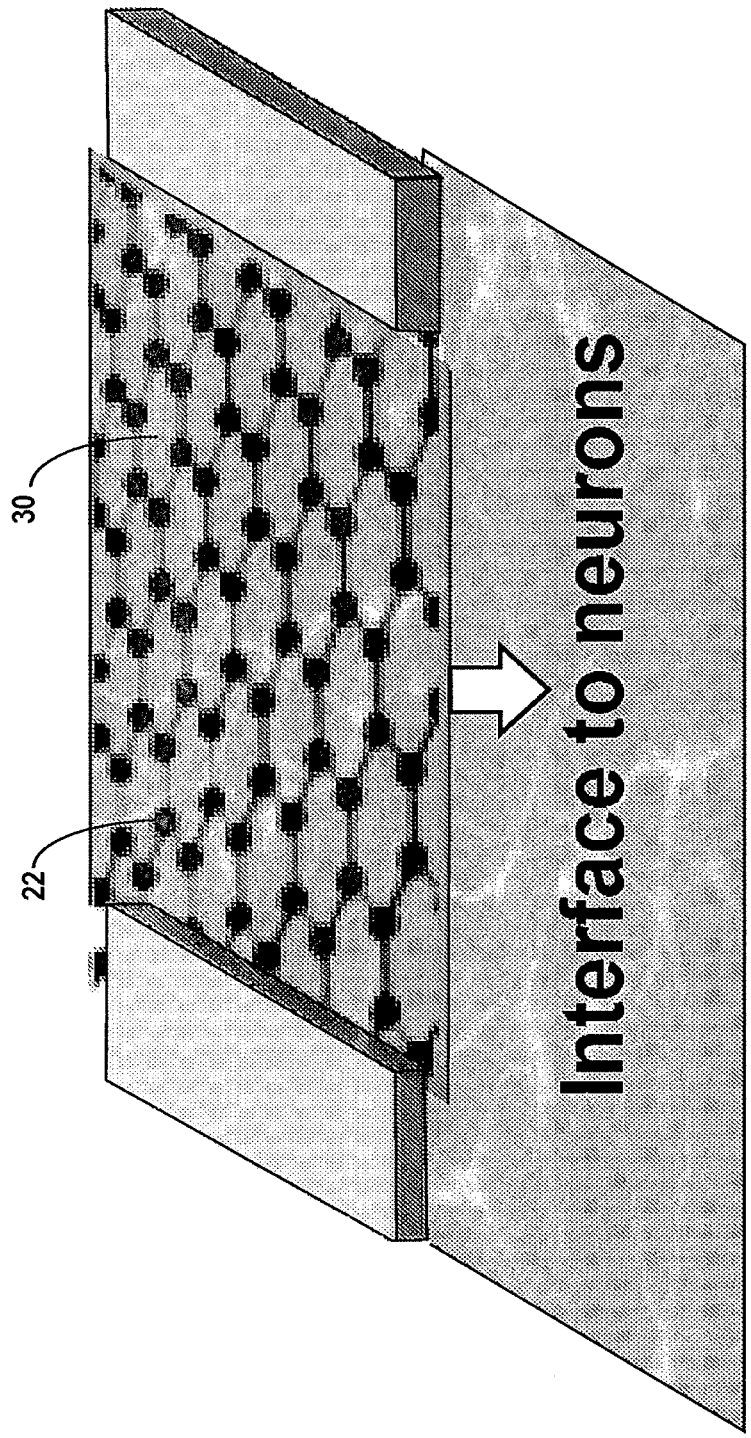
FIG. 2 shows a high sensitivity, ultra-low power, high SNR, and high speed graphene field effect transistor (GFET) sensor for neural activity recoding in accordance with the present disclosure.

To enable flexible and bio-compatible high-performance sensors within a desired power budget, graphene field effect transistor (GFET) based neuroelectric sensors 22 on a biocompatible microbial cellulose (MBC) membrane 30, as shown in FIG. 2, are used to record in vivo neuronal spikes and the resulting local field potential (LFP) with high temporal resolution (<1 µs). Graphene is a single atom-thin sp$^2$ carbon layer, which is stable in air and potentially stable in vivo with a flexibility of up to 18% strain. High sensitivity and biocompatibility of graphene-based biosensors have been reported previously, as described in References 19-21 below. It has also been demonstrated that young and adult neurons survive and grow neuritis on graphene, confirming a potential for bio-compatibility, as described in Reference 22 below. Preliminary recording of activities of HL-1 human cells using GFETs has been reported with transconductance $(g_m)'$ of 10 mS/mm at $V_{ds}$=50 mV, as described in Reference 23 below.

With very high electronic mobility (>1000 cm$^2$/Vs compared to 0.5 cm$^2$/Vs of PEDOT transistors), the source-drain current $(I_{ds})$ of GFETs is very sensitive to modulation by the gate potential $(V_{gs})$, as indicated by its high $g_m$. $g_m$ equals $dI_{ds}/dV_{gs}$: a measure of how sensitive drain current $(I_{ds})$ changes with gate voltage. Embodiments according to the principles of the present invention provide an n-channel $g_m$ of GFET is ~70 mS/mm at very small $V_{ds}$, =50 mV even with 30 nm SiO$_2$ gate oxide, and as described in Reference 24 below. The highest $g_m$ in GFETs has been reported to reach 1050 S/mm at $V_{ds}$=1 V, as described in References 25 and 26 below. GFETs have the lowest ohmic contact resistance reported to date, as described in Reference 27 below. This leads to the lowest measured source-drain current noise spectral power, $S_i$, below 10$^{-19}$ A$^2$/Hz at 10 Hz, as described in Reference 28 below. This results in <1 µV input voltage noise, which is much smaller than the neural potential, which averages around a few millivolts. With a 1-mV spike voltage, the current 10 µm-wide GFET sensor produces ~800 nA with a background current noise of 25 nA when the sensor is biased at $V_{ds}$=50 mV. The signal-to-noise ratio (SNR) of the GFET is 30 dB and the total power consumption is ~20 µW. GFET sensors may be fabricated with an ultra-thin gate oxide (<3 nm) layer or without any gate oxide layer, which improves $g_m$ and sensitivity by more than 10 times. This results in a SNR of >50 dB at the same power of 20 µW or SNR of ~30 dB at 1 µW total power consumption. The maximum recording distance, $r_{max}$ of a sensor or a measuring electrode, is estimated with $r_{max} \approx r_0 \times \ln(\text{SNR})$, where $r_0$ is 1/e fall-off distance of (voltage) signal of a neuron spike in the brain and a measured value of $r_0$~28 µm. Assuming SNR ~50 dB, the maximum recording distance $(r_{max})$ of the GFET sensor is $r_{max}$ ~300 µm, compared to $r_{max}$~130 µm of a conventional MEA, as described in Reference 1 below.

With reference to FIG. 2 the GFET sensor arrays 22 may be fabricated with a linear pitch of 50 µm (25 µm pitch feasible), which can result in an 8:1 ratio of neuron cells to sensors, assuming one neuron in every 25 µm voxel of a mouse brain.

Continuing with FIG. 2 the microbial cellulose (MBC) films 30 are bio-compatible, bio-permeable and ultra-flexible when wet but become rigid when dry. MBC films 30 are used as substrates for the unique benefits that they provide: cell attachment and proliferation, high wet strength with tensile strength ~196.6 MPa and Young's modulus ~21.0 GPa, and biocompatibility with no immunological reactions reported to date, high purity, high crystallinity, nanometer-scale fibril diameters, and the ability to absorb and hold large quantities of water. Prof. H.-J. Jin at the department of Polymer Science and Engineering at Inha University in South Korea has performed MBC research for over 10 years and has well-developed MBC processes, as described in References 29-33 below, that may form suitable MBC substrates. Extensive research on biomedical applications of MBC including tissue engineering/regeneration, replacement for dura mater, and orthopedic applications has been reported, as described in References 34-37 below. The application of MBC films as substrates for microelectronic devices including supercapacitors, OTFT, OLED, and display devices has been demonstrated recently, with good adhesion of metal contacts on MBC, as described in References 38-43 below.

Figure 4:
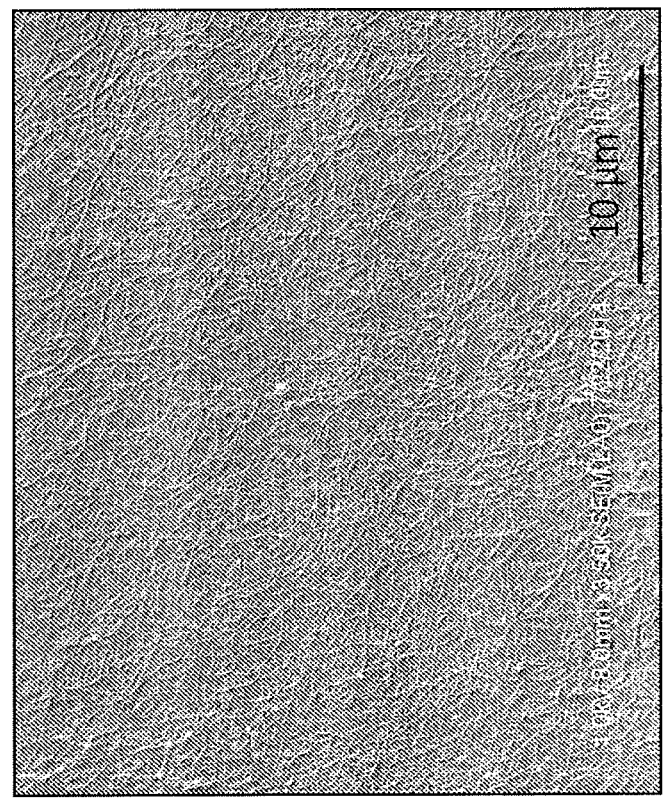
FIG. 4 shows a SEM image of MBC films in accordance with the present disclosure.
Figure 3:
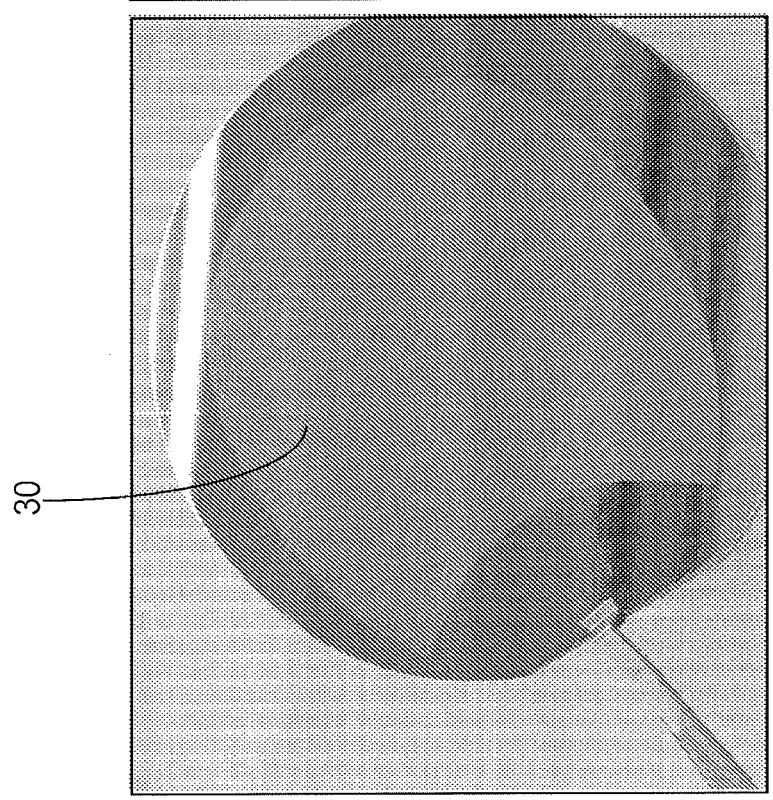
FIG. 3 shows a microbial cellulose (MBC) to be used as a substrate for a biocompatible wireless neuroelectric sensor and stimulator arrays in accordance with the present disclosure.

FIG. 3 shows a microbial cellulose (MBC) 30 to be used as a substrate for a biocompatible wireless neuroelectric sensor and stimulator array 10, and FIG. 4 shows a SEM image of MBC films.

An ~10 µm thick MBC 30 is used as a substrate for WINSS for a proof-of-concept demonstration; however, MBC membranes 30 can be grown as thin as ~1 µm. For WINSS micro-strips that are inserted into the brain for depth analysis, if the substrate is desired to be dissolved after implantation, MBC composites (e.g., with poly(L-lactic acid)), as described in Reference 30 below, can be used for a substrate.

FIGS. 5A, 5B, 5C, 5D, 5E, and 5F show a process flow for fabricating a graphene-based neuroelectric sensor 22 in accordance with the present disclosure. Fabrication of a GFET based neuroelectric sensor begins with a bio-compatible microbial cellulose (MBC) membrane 30 mounted on a handling wafer 32, which may be Si or glass. Then the MBC membrane 30 is passivated with an atomic layer deposition (ALD) of dielectric 34 or a bio-compatible thin polymer layer 34, for example SU8, to protect the MBC 30 and to control its water intake during fabrication, as shown in FIG. 5A. Chemical vapor deposition (CVD) grown graphene 36 is then transferred over the passivated MBC, as shown in FIG. 5B. Next the transferred CVD graphene 36 is patterned using lithography or any other well known patterning method, followed by oxygen plasma etching to form graphene mesa structures 38, which may be about ~10×10 µm in area, as shown in FIG. 5C. Ohmic contacts for source and drain electrodes 40 may be made over the graphene mesas 38 using a biocompatible Ti alloy, and contacts for an electrical ground 42 and a multiplexer 44 may also be fabricated using biocompatible metals or metal alloys, as shown in FIG. 5D. An optional gate electrode integrated with a gate dielectric may also be fabricated using a biocompatible metal or a metal alloy. The source and drain electrodes 40, electrical contacts for multiplexer 44 and electrical ground 42, and the optional gate electrode may be passivated with a biocompatible polymer. Next, etching may optionally be performed to remove the ALD dielectric 34 or the bio-compatible polymer layer 34 from the background nonactive area 41 of the sensor stimulator system, as shown in FIG. 5E. Then the MBC membrane 30 may be released from the handling wafer 32, as shown in FIG. 5F.

Transfer processes have been demonstrated for CVD graphene to non-native substrates, including flexible substrates, such as polyethylene terephthalate (PET), Polyethylene naphthalate (PEN), or flexible glass, and carrier mobilities of ~1000 $cm^2/Vs$ have been measured, which is >10× higher than other electronic materials on flexible substrates. Using transferred CVD graphene, graphene FETs and varactors have been demonstrated on flexible substrates that operate in the RF range. FIG. 6A shows a SEM image of CVD graphene transferred over a silver nanowire network, FIG. 6B shows a SEM image of CVD graphene transferred over a passivated MBC film, FIG. 6C shows a SEM image of CVD graphene transferred over a 1-µm-high metal contact, and FIG. 6D shows a photograph of graphene active devices fabricated on a PET substrate.

Nanocellulose fibrils in MBC have diameters of ~100 nm and lengths of tens of µm, which is very similar to the dimensions of silver nanowires. Previously, a process for transferring CVD grown graphene onto silver nanowire networks has been developed, as shown in FIG. 6A and U.S. patent application Ser. No. 14/530,365 filed Oct. 31, 2014 titled "All-wavelength (Vis-LWIR) transparent electrical contacts and interconnects and methods of making them" incorporated by reference as though fully set forth herein. This process may be utilized for graphene 36 transfer onto the MBC membrane 30. The ALD dielectric passivation layer 34 may be thin (~10 nm) and reduces any MBC 30 induced charge trapping and detrapping, which would otherwise be an origin of 1/f noise. MBC can be also passivated with a bio-compatible polymer 34, such as SUB, which can serve as a barrier to moisture and water and also provides a smooth surface critically needed for microfabrication of graphene neuroelectric sensors.

Figure 7:
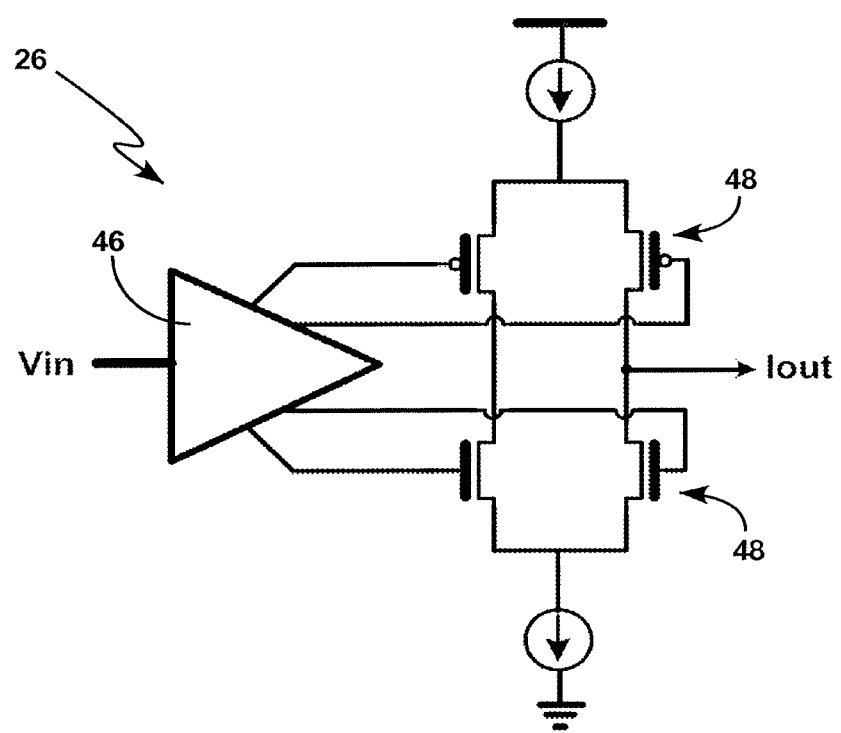
FIG. 7 shows a schematic of a graphene-based neural stimulator circuit in accordance with the present disclosure.

A neuron stimulator needs to provide a dedicated current pattern to stimulate the neurons, such as biphasic stimulus, as described in References 44 and 45 below. In WINSS, the neuroelectric sensor and stimulator array 10 (shown in FIG. 1) receives the stimulus pattern from the external reader 12 and synthesizes the desired current pattern through a low-power analog signal processor. The stimulation driver 24 must provide a high fidelity current conversion. FIG. 7 shows one embodiment of a graphene based neural stimulator driver circuit 24. The circuit may include a high gain operational amplifier 46, and a differential amplifier 48 to achieve a desired fidelity, both of which may be implemented with graphene based transistors.

The WINSS includes high-data-rate, ultra-low-power radio frequency RF links with a semi-passive data acquisition and stimuli approach. The RF links achieve a desired low-power operation with low bit error rate, by incorporating 1) a semi-passive microwave (~GHz) RFID architecture, 2) high mobility (>1000 $cm^2/Vs$) graphene transistors and envelope detectors on flexible/bio-compatible substrates, and 3) normally-off graphene heterostructure transistors for signal multiplexing. The RF links also provide a scalable solution to achieve large-scale probing for the targeted spatial and temporal resolutions.

Figure 8:
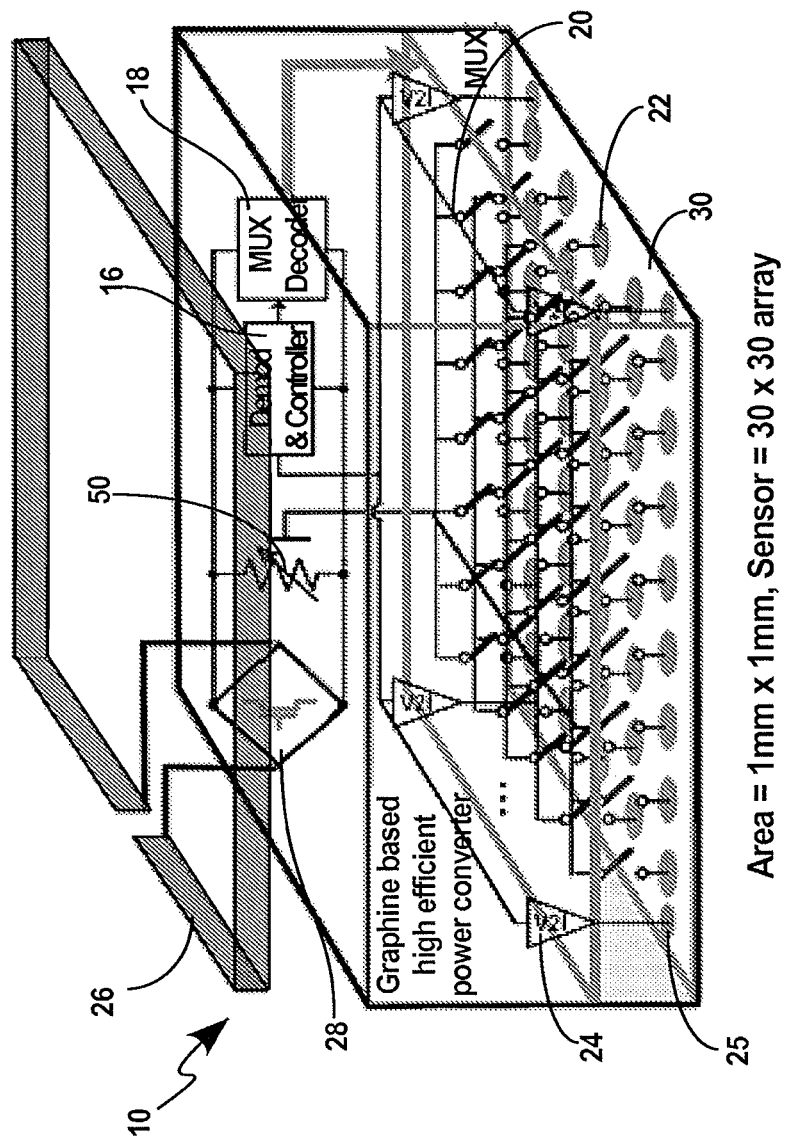
FIG. 8 shows a detail of FIG. 1 for the sensors and stimulators of a brain sensing and wireless link according to the present disclosure.
Figure 9:
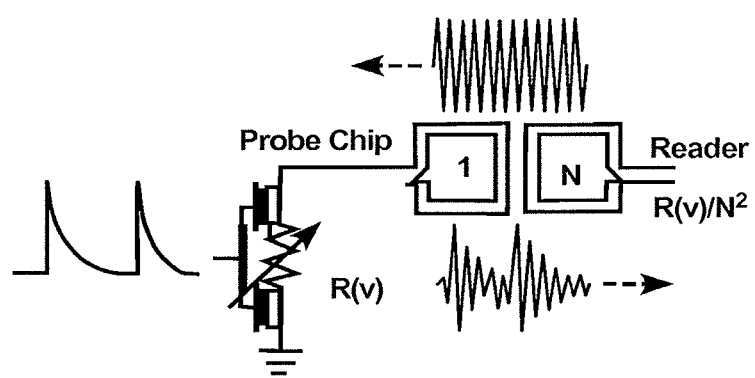
FIG. 9 shows the load modulation reflector based on analog transmission in accordance with the present disclosure.

FIG. 8 shows a detail of one array of neuroelectric sensors and stimulators 10, which may be integrated onto a single chip. A single graphene transistor based rectifier 28 is used to convert the alternating current (AC) signal received by the antenna 26 into a direct current (DC) supply that can be used by on-chip components of the neuroelectric sensor stimulation array 10. Details of rectifier 28 are known to those skilled in the art and illustrations herein are not to be construed as limiting. The antenna 26 may be integrated on the single chip so that it is an on chip antenna. A demodulator and controller 16, and a mux decoder 18 are connected to one another and to antenna 26 and are used to determine a reading sequence for reading the sensors 22 in the neuroelectric sensor stimulator array 10 and for controlling stimulators 24. A multiplexer 20 connects to the array of sensors 22. Control from the mux decoder 18 sets the state of the multiplexer 20, so that one sensor 22 at a time may be read. A voltage controlled resistor 50 whose resistance can be programmed by an external voltage may be used to adjust the power from the sensors 22. The demodulator and controller 16 is connected to antenna 26 and to voltage to current (V2I) blocks 24, which convert received voltage information to a current signal to stimulate neurons in the brain. The voltage to current (V2I) blocks 24 are connected to stimulator pads 25, which may be integrated onto biocompatible microbial cellulose (MBC) membrane 30.

When the transmission data rate is >100 MHz, antennas separate from antenna 26 or separate from antennas 14 and 26, may be used at RF frequency to transmit high-speed data back to the reader. A separate antenna inside the brain may also be an on chip antenna, similar to antenna 26.

Embodiments according to the principles of the present invention shown in FIG. 8 have the following advantages. First, the neuron firing signals are sensed and sampled in analog form and not converted to digital form in the implantable WINSS chips with the sensor stimulator array 10, which removes the need for an ADC, which normally consumes significant power. The demodulator and controller 16, and MUX decoder 18 operate at a low clock rate and consume only dynamic power. Also, because major blocks of the circuit, such as the multiplexer 20, are controlled by a voltage and do not consume power except through leakage, the implementation is a semi-passive implementation with low power. The total power consumption for a neuroelectric sensor stimulator array 10 is only at only micro watt (µW) levels.

Second, the signals transmitted between the antenna 14 and the antenna 26 are in analog form, which greatly reduces the required transmission bandwidth. For example, conventional neural probes often digitize the sampled signal into 6 bits or more and transmit them between the probe chip and the outside reader. Using analog transmission, the transmission speed is reduced by a factor of six. Given the same system temporal resolution with identical transmission speeds, Embodiments according to the principles of the present invention have a higher multiplex ratio and transmit more neuron activities, therefore increasing system spatial resolution.

Third, the graphene FET (GFET) based envelope detectors of FIG. 10 consume negligible power and feature high fidelity and passive data demodulation, as described in Reference 46 below.

Fourth, the unique ambipolar properties of graphene transistors enable a highly efficient power rectifier 28 by using a single graphene transistor in contrast to conventional four-diode full bridges, as described in Reference 42 below. Because the voltage drop across the rectifier is reduced in half, the wireless power rectification efficiency is drastically improved.

Embodiments according to the principles of the present invention leverage the unique characteristics of graphene transistors, such as a relatively linear relation between transistor channel resistance and gate control voltage of graphene transistors, to enable analog information transmission. The ambipolar property of graphene transistors provides high power conversion and data demodulation efficiency, to shift the signal processing burden from the implantable probe circuit to outside readers. Embodiments according to the principles of the present invention have relaxed power consumption and scaling requirements, which simplifies the probe circuit and makes it easily scalable by enabling smaller form factors and low-power implementations. Hence, the approach can support large-area deployment for high-density monitoring.

The power consumption for the array 10 according to the principles of the present invention has been compared to a typical CMOS monitoring chip implementation and to Tucker's limit, as described in Reference 47 below. The CMOS implementation demonstrates high power consumption when the number of neurons increases above 10,000. This is because the CMOS implementation uses active circuits that consume power, which also increases with the number of neurons. In contrast, the graphene implementation according to the principles of the present invention features a semi-passive implementation. Although the multiplexer 20 scales linearly with the number of neurons, it remains passive and does not consume power except via leakage. The mux decoder 18 scales with the square root of the number of neurons. The other blocks do not scale with the number of neurons. The result is a system with overall favorable scaling.

To ensure high quality neuron activity recording, the system must consume <40 mW/cm$^2$, as described in Reference 1 below. Given the population of one neuron per 25 μm voxel, the requirement can be interpreted as 40 mW/160,000 neurons. The semi-passive graphene-based array 10 consumes <4 mW for 160,000 neurons, which meets the system requirements. Compared with Tucker's limit, which is described in Reference 47 below, the array 10 still demonstrates four orders of magnitude higher power consumption with a large number of neurons. This is mainly due to the power lost due to leakage in the transistors and power consumed in peripheral circuits, which have not been considered by Tucker, et al.

Figure 10:
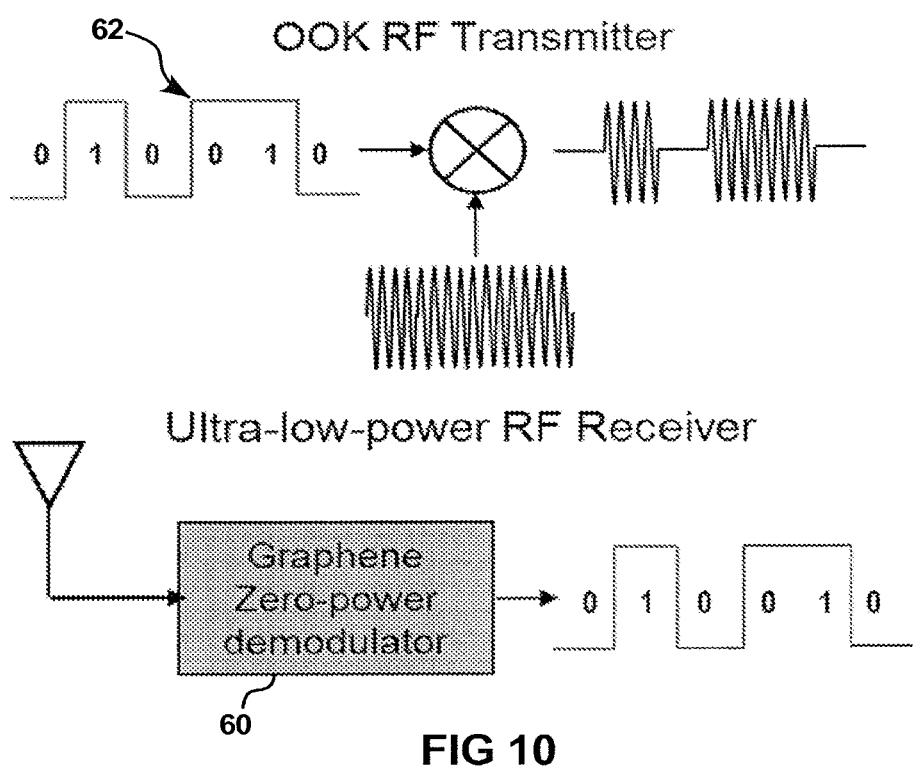
FIG. 10 shows a block diagram of the ultra-low-power receiver with a graphene zero-bias envelope detector, which demodulates the On-Off-Key (OOK) waveform to recover the data rate, in accordance with the present disclosure.

FIG. 10 shows the current-voltage characteristics of a A normally-off (enhancement mode) graphene heterostructure transistor (HFET) may have a leakage current <30 pA/um. For an implementation with 10-um-wide graphene HFETs, a 1000:1 multiplexer 20 has a power consumption of <0.3 nW. Preliminary simulated results indicate that graphene-based MUX decoders 18 consume <1 uW of dynamic power when switching at 1 kHz. This data is used to predict the system power consumption as less than 4 mW.

The measured channel resistance of a graphene transistor compared to a typical MOS transistor under control voltage, respectively has a linear resistance. This characteristics enables analog transmission based on a load modulation reflector, which modulates the resistance with an analog signal, which in turn varies the load resistance perceived by the reader 12. An analog load modulation-based reflector is used to transmit the signal from the WINSS array chip 10 to the external reader. Due to the linear channel resistance of graphene transistors, multiple graphene transistors can be combined in series to form a large resistor on the probe chip. With different gate control voltage v, the resistor presents a resistance R(v). Assuming the antenna 14 and the antenna 26 are coupled together with a coupling ratio N, the voltage control resistance R(v) is seen by the reader 12 to be the value of $R(v)/N^2$. Therefore, a high-frequency signal sent from the reader 12 to the WINSS array chip 10 is modulated by the varied R(v) and presents a voltage envelope to the reader 12, which can be analyzed by an off-site, high-speed, high-dynamic-range ADC such as 14 bit and 65 Ms/s LTC2258 part inside the reader. This is equivalent to the array chip 10 reflecting the signal back to the reader 12 with a modulated envelope. This approach brings two significant advantages. First, the analog modulation-based reflector compresses the information into a narrow band to reduce the communication bandwidth, and second, analog transmission removes the need for an on-chip ADC, therefore reducing power consumption. The reader 12 does need a high-resolution ADC; however, the reader 12 is outside the brain and the power budget of the reader need not be constrained.

FIG. 10 shows a block diagram of an ultra-low-power demodulator 16 (in FIG. 1) with a graphene zero-bias envelope detector 60, which demodulates the On-Off-Key (OOK) waveform 62 to recover the data rate. The measured eye diagram of the OOK envelope at 20 Mb/s data rate at 3 GHz, showed clear communication at 20 Mb/s. The rise time was about 20 nsec. The measured graphene envelope detectors demonstrated >40 dB dynamic range with −60 dBm sensitivity.

The WINSS may be powered wirelessly via inductive RF coupling at a frequency of 100 MHz or higher. Many inductive RF links have been demonstrated with excellent efficiency. At 1000 μW power transfer, the overall link efficiency may be 67% to 51% with 1 mm and 10 mm physical separation of antenna 14 and antenna 26 running at 4.5 MHz. as described in Reference 48 below.

Figure 11:
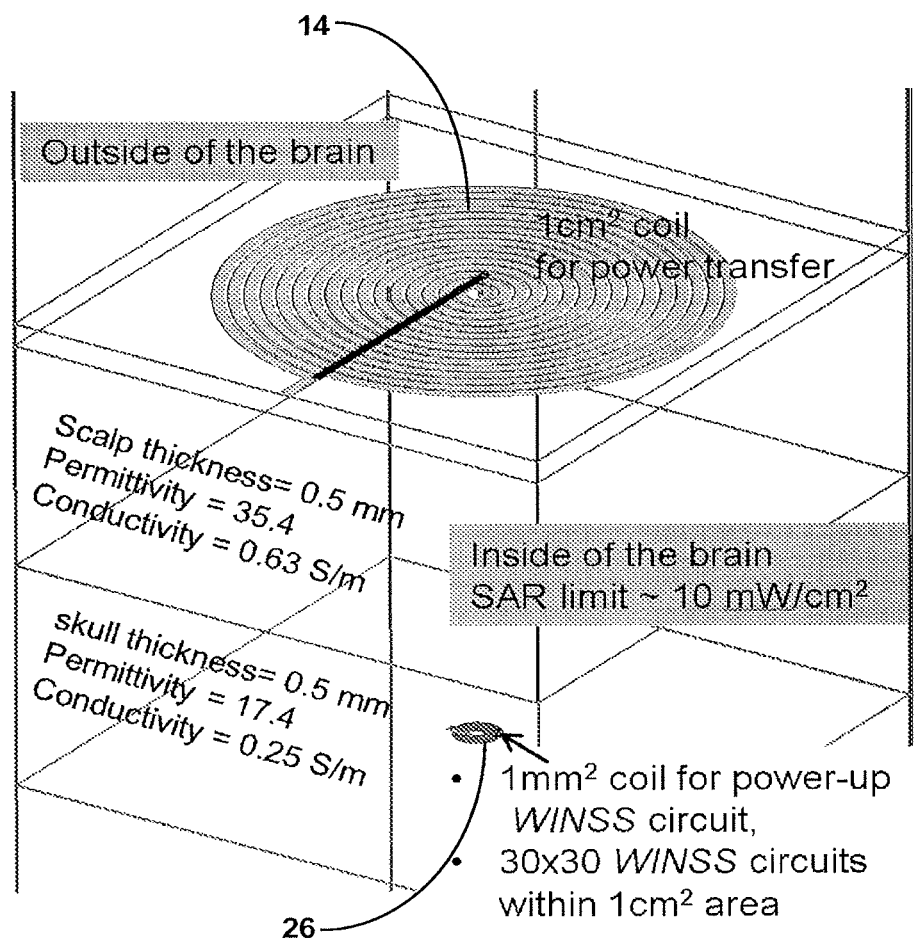
FIG. 11 shows the conditions for a simulation of inductive wireless power transfer between a 1 $cm^2$ transmitting coil outside of the brain and 1 $mm^2$ receiving coil inside of the brain within the brain specific absorption rate (SAR) limit in accordance with the present disclosure.

FIG. 11 shows the conditions for a simulation of inductive wireless power transfer between a 1 cm$^2$ transmitting antenna 14, which may be a coil, outside of the brain and 1 mm$^2$ receiving antenna 26, which may also be a coil, inside of the brain within the brain specific absorption rate (SAR) limit. These simulations show that power can be delivered to neuroelectric sensor stimulator arrays 10 within the brain's specific absorption rate (SAR) limit of ~10 mW/cm$^2$.

Neuronal recording requires attributing observed spiking activity with the neurons that fired them, otherwise known as spike sorting. In the ideal case, a spike fired from one neuron would appear on only one sensor or electrode in a multi-electrode array (MEA). There would be a 1:1 map between electrodes and neurons being monitored. In reality, each spike is detected by multiple electrodes, and similarly, multiple spikes fired by different neurons appear on each electrode of the MEA. The sensing of multiple firing neurons is often referred to as multi-unit recording. The signal processing problem is to decipher these combinations of spikes on every electrode and properly associate each spike with its source neuron, i.e., to find single-unit activity.

While many neuroscientists rely on manual spike sorting techniques (e.g., spike amplitude thresholding), there are significant efforts in developing automated methods. Prior art algorithms include using spike templates or clustering. Others have looked into using principal component analysis (PCA) and independent component analysis (ICA) to sort spikes. Each has its merits and disadvantages. Templates can be very effective at sorting spikes but require a learning period for automation and are computationally heavy as spike waveforms on each electrode are compared to those in a template database. As spike waveforms change over time, the template database must also be refreshed regularly. PCA is very simple to implement but is ineffective at deciphering combinations with time overlapping spike waveforms. ICA, while very effective at separating spikes, can be computationally taxing and does have assumptions to its applicability which need to be understood, such as the simultaneous appearance of spike waveforms on every electrode. Clustering can be fast and energy efficient, but requires knowledge of the number of different spike waveforms to expect; an inaccurate assumption of the number of waveforms can lead to the algorithm breaking down. Like PCA, clustering is not used to separate spikes that overlap in time. However, clustering can be combined with deconvolution methods, as described in Reference 49 below, which require knowing the spike shapes, to separate time-overlapping spike waveforms.

Another algorithm that has also gained some interest is the Multiple Signal Classification (MUSIC) algorithm. MUSIC is used to extract the frequency components of a signal in the presence of white noise. MUSIC accomplishes the extraction of signals in a linear combination by turning the separation problem into an eigenvalue problem and isolating eigenvectors with the largest eigenvalues. While not as sophisticated as ICA, it is computationally simpler and leads to low-power implementations. It also requires the simultaneous appearance of spikes on the various electrodes.

The present disclosure uses a combination of a signal separation algorithm, such as MUSIC, to separate the individual spike trains, and reconfiguring the sampling rate of the MEA on selective sensors to track the spatial evolution of specific spike waveforms, followed by progressive stimulation using multiple low-field stimulators to determine thresholds for specific neurons.

The method has several advantages. First, the eigenvalue decomposition method allows for the separation of spike waveforms without a template or learning period, even with time-overlapping spikes. There is no re-calibration phase to re-learn the spike waveforms as they change over time. Second, increasing the sampling rate (from 10 kHz to 1 MHz) on fewer sensors (10× fewer) trades off sensing area with time resolution without requiring extra hardware, permitting higher temporal resolution focused on specific regions to track the spike as it moves along the axon. Switching off unused sensors maintains the aggregate bandwidth. Third, progressively increasing the amplitude of specific stimulators and observing when a desired spike waveform is emitted gives the approximate threshold for the firing neuron. Low-voltage stimulation emits an electric field which decays exponentially in the medium. The simultaneous low-voltage activation of multiple stimulators keeps the fields low in most of the extracellular medium with a higher field in the region of intersection. The spatial combining of the fields provides local stimulation to regions of interest. The gradual increase in stimulator power lets us detect an upper bound to the activation threshold of the firing neurons in the region, as there is some uncertainty to the amount of exponential decay between the stimulators and neurons.

In summary, the Scalable Wireless Neuroelectric Sensor and Stimulator Arrays System (WINSS) according to the principles of the present invention provides the following features. A high-speed, ultra-low power, and high-sensitivity graphene-based neuroelectric sensor array 22, a scalable high-density nanosensor network fabricated on a microbial cellulose platform 30, neuron stimulators 24 monolithically integrated in a sensor node with high-speed sampling capability, a brain-compatible ultra-low-power RF electronics and wireless communication link, and a highly efficient inductive RF energy transfer using a graphene rectifier 28.

REFERENCES

The following references are incorporated by reference as though set forth in full.
1. Marblestone A H, Zamft B M, Maguire Y G, Shapiro M G, Cybulski T R, Glaser J I, Amodei D, Stranges P B, Kalhor R, Dalrymple D A, Seo D, Alon E, Maharbiz M M, Carmena J M, Rabaey J M, Boyden E S, Church G M, and Kording K P "Physical principles for scalable neural recording", Frontiers in Computational Neuroscience 7, 1 (2013).
2. Berényi A, Somogyvari Z, Nagy A J, Roux L, Long J D, Fujisawa S, Stark E, Leonardo A, Harris T D, and Buzsaki G, "Large-scale, high-density (up to 512 channels) recording of local circuits in behaving animals", Journal of Neurophysiology DOI: 10.1152/jn.00785.2013 (2013).
3. Frewin C L, Locke C, Mariusso L, Weeber E J, Saddow S E, "Silicon carbide neural implants: in vivo Neural tissue reaction", Engineering in Medicine and Biology Science, EMBC 2013, Annual International Conferences of the IEEE, San Diego, Calif., 2013 pp. 661.
4. Abdelhalim K, Jafari H M, Kokarovtseva L, Velazquez J L P, Genov R "Neural Synchrony-Monitoring Wireless Brain Implant for Intractable Epilepsy Neuromodulation", Engineering in Medicine and Biology Science, EMBC 2013, Annual International Conferences of the IEEE, San Diego, Calif., 2013 pp. 65.
5. Agha N S, Komar J, Yin M, Borton D A, and Nurmikko A, "A Fully Wireless Platform for Correlating Behavior and Neural Data from an Implanted, Neural Recording Device: Demonstration in a Freely Moving Swine Model", Proceedings of Engineering in Medicine and Biology Science, EMBC 2013, Annual International Conferences of the IEEE, San Diego, Calif., 2013 pp. 989.
6. Borton D A, Yin M, Aceros J, and Nurmikko A, "An implantable wireless neural interface for recording cortical circuit dynamics in moving primates", Journal of Neural Engineering, 10, 026010, (2013).
7. Seo D, Carmena J M, Rabaey J M, Alon E, and Maharbiz M M, "Neural Dust: An Ultrasonic, Low Power Solution for Chronic Brain-Machine Interfaces", arXiv:1307.2196 [q-bio.NC] (2013).
8. Castagnola E, Maiolo L, Maggiolini E, Minotti A, Marrani M, Maita F, Pecora A, Angotzi G N, Ansaldo A, Fadiga L, Fortunato G, Ricci D, "Ultra-flexible and brain-conformable micro-electrocorticography device with low impedance PEDOT-carbon nanotube coated microelectrodes", Engineering in Medicine and Biology Science, EMBC 2013, Annual International Conferences of the IEEE, San Diego, Calif., 2013 p. 927.
9. Cogan S F, Troyk P R, and DeMichele G, "Stability of Thin-film Wireless Recording and Stimulation Devices for Epilepsy Monitoring", Engineering in Medicine and Biology Science, EMBC 2013, Annual International Conferences of the IEEE, San Diego, Calif., 2013 p. 1005.
10. http://www.neuronexustech.com/11.
11. Khodagholy D, Doublet T, Quilichini P, Gurfinkel M, Leleux P, Ghestem A, Ismailova E, Herve T, Sanaur S, Bernard C, & Malliaras G G, "In vivo recordings of brain activity using organic transistors", Nature Communications 4, 1575 (2013). DOI: 10.1038/ncomms2573.
12. Sarpeshkar R. "Ultra Low Power Bioelectronics" New York, N.Y.: Cambridge University Press. doi: 10.1017/CBO9780511841446 (2010).
13. Gittis A H, Moghadam S H, and du Lac S, "Mechanisms of sustained high firing rates in two classes of vestibular nucleus neu-rons: differential contributions of resurgent Na, Kv3, and BK currents", J. Neurophysiol. 104, 1625 (2010). doi: 10.1152/jn.00378.2010.
14. Wolf P D, "Thermal considera-tions for the design of an implanted cortical brain-machine interface (BMI)," in Indwelling Neural Implants: Strategies for Contending with the In Vivo Environment, ed W. M. Reichert (Boca Raton, Fla.: CRC Press) (2008).
15. Liu L C, Ho M H, and Wu C Y, "A medradio-band low-energy-bit CMOS OOK transceiver for implantable medical devices", IEEE Biomedical Circuits and Systems Conference, pp. 153-156, (2011).
16. Biederman W, Yaeger D J, Narevsky N, Koralek A C, Carmena J M, Alon E, et al. "A fully-integrated, miniaturized (0.125 mm$^2$) 10.5 µW wireless neural sensor", IEEE J. Solid-State Circuits 48, 960. doi: 10.1109/JSSC.2013.2238994 (2013).
17. Myny K, Steudel S, Smout S, Vicca P, Furthner F, van der Putten B, Tripathi A K, Gelinck G H, Genoe J, Dehaene W, and Heremans P, "Organic RFIC transponder chip with data rate compatible with electronic product coding", Organic Electronics vol. 11, pp. 1176-1179, (2010)
18. Dagdeviren C, Hwang S W, Su Yewang, Kim S, Cheng H, Gur O, Haney R, OMenetto F G, Huang Y, and Rogers J A, "Transient, Biocompatible Electroncis and energy harvesters based on ZnO", Small, vol. 9, pp. 3398-3404, (2013)
19. Cohen-Karni T, Qing Q, Li Q, Fang Y, and Lieber, C M, "Graphene and Nanowire Transistors for Cellular Interfaces and Electrical Recording", Nano Lett. 10, 1098 (2010).
20. Shen H, Zhang L, Liu M, Zhang Z, "Biomedical Applications of Graphene", Theranostics 2, 283 (2012).
21. Shao Y, Wang J, Wu H, Liu J, Aksay I A, Lina Y, "Graphene Based Electrochemical Sensors and Biosensors: A Review", Electroanalysis 22, 1027 (2010).
22. Bendali A, Hess L H, Seifert M, Forster V, Stephan A-F, Garrido J A, and Picaud S, "Purified Neurons can Survive on Peptide-Free Graphene Layers", Advanced Healthcare Materials 2, 929 (2013)
23. Hess L H, Seifert M, Garrido J A, "Graphene transistors for bioelectronics", Proceedings of the IEEE 101, 1780 (2013).
24. Moon J S, Seo H C, Stratan F, Antcliffe M, Schmitz A, Ross R S, Kiselev A A, Wheeler V D, Nyakiti L O, Gaskill D K, Lee K M, and Asbeck P M, "Lateral Graphene Heterostrucure FETs", IEEE Electron Device Letters 34, 1190 (2013).
25. Moon J S, Curtis D, Bui S, Hu M, Gaskill D K, Tedesco J L, Asbeck P, Jernigan G G, VanMil B L, Myers-ward R L, Eddy C R Jr., Campbell P M, and Weng X, "Top-gated Epitaxial graphene FETs on Si-face SiC wafer with a peak transconductance of 600 mS/mm", IEEE Electron Device Letters, vol. 31, pp. 260-262 (2010)
26. Moon J S, "Advances in graphene R F electronics" (Invited), Proceedings of International Microwave Symposium (2013).
27. Moon J S, Antcliffe M, Seo H C, Curtis D, Lin S, Schmitz A, Milosavljevic M, Kiselev A A, Ross R S, Gaskill D K, Campbell P M, Fitch R C, Lee K M, and Asbeck P, "Ultra-low ohmic contacts to graphene FETs", Applied Physics Letters 100, 203512 (2012)
28. Moon J S, Curtis D, Zehnder D, Kim S, Gaskill D K, Jernigan G G, Myers-ward R L, Eddy C R Jr., Campbell P M, Lee K M, and Asbeck P, "Low-phase-noise graphene FETs in ambipolar RF applications", IEEE Electron Device Letters 32, 270 (2011).
29. Chen P, Cho S Y, and Jin H-J, "Modification and Applications of Bacterial Celluloses in Polymer Science", Macromolecular Research 18, 309 (2010). DOI 10.1007/s13233-010-0404-5.
30. Kim Y, Jung R, Kim H-S, Jin H-J, "Transparent nanocomposites prepared by incorporating microbial nanofibrils into poly(L-lactic acid)", Current Applied Physics 9, S69 (2009).
31. Park W-I, Kim H-S, Kwon S-M, Hong Y-H, Jin H-J, "Synthesis of bacterial celluloses in multiwalled carbon nanotube-dispersed medium", Carbohydrate Polymers 77, 457 (2009).
32. Jung R, Kim Y, Kim H-S, and Jin H-J, "Antimicrobial Properties of Hydrated Cellulose Membranes With Silver Nanoparticles", Journal of Biomaterials Science 20, 311 (2009).
33. Jung R, Kim H-S, Kim Y, Kwon S-M, Lee H S, Jin H-J, "Electrically Conductive Transparent Papers Using Multiwalled Carbon Nanotubes", Journal of Polymer Science: Part B: Polymer Physics 46, 1235 (2008).
34. Fu Lina, Zhang Yue, Zhang Jin and Yang Guang, "Bacterial Cellulose for Skin Repair Materials", Chapter 13 of Biomedical Engineering—Frontiers and Challenges, book edited by Reza Fazel-Rezai (2011), ISBN 978-953-307-309-5. DOI: 10.5772/24323
35. Dugan J M, Gough J E, Eichhorn S J, "Bacterial Cellulose Scaffolds and Cellulose Nanowhiskers for Tissue Engineering", Nanomedicine 8, 297 (2013).
36. Fernando G. Torres, Solene Commeaux, and Omar P. Troncoso, "Biocompatibility of Bacterial Cellulose Based Biomaterials", J. Funct. Biomater 3, 2012, 3, 864 (2012). doi:10.3390/jfb3040864.
37. Czaja W K, Young D J, Kawecki M, and R. Malcolm Brown R M, Jr., "The Future Prospects of Microbial Cellulose in Biomedical Applications", Biomacromolecules 8, 1 (2007).
38. Kang Y J, Chun S-J, Lee S-S, Kim B-Y, Kim J H, Chung H, Lee S-Y, and Kim W, "All-Solid-State Flexible Supercapacitors Fabricated with Bacterial Nanocellulose Papers, Carbon Nanotubes, and Triblock-Copolymer Ion Gels", ACS Nano 6, 6400 (2012).
39. Pereira A T, Ferreira Q, Freire C S R, Fernandes S C M, Trovatti E, Neto C P, Silvestre A J D, Morgado J, Luis Alcácer L, "Bacterial cellulose as substrate for inkjet printing of organic thin film transistors", ICOE 2012 ABSTRACT.
40. Legnani C, Vilani C, Calil V L, Barud H S, Quirino W G, Achete C A, Ribeiro S J L, Cremona M, "Bacterial cellulose membrane as flexible substrate for organic light emitting devices", Thin Solid Films 517, 1016 (2008).
41. Alcacer L, Morgado J, Ferreira Q, Pecoraro E, Neto C P, Silvestre A J D, Freire C S R, Trovatti E, Fernandes S C M, "Biocellulose Based Materials for Organic Field Effect Transistors" Proc EUROCON and CONFTELE 2011, Lisbon, Portugal, April, 2011
42. Gaspar D, Fernandes S N, Oliveira A G de, Fernandes J G, Grey P, Pontes R V, Pereira L, Martins R, Godinho M H and Fortunato E, "Nanocrystalline cellulose applied simultaneously as the gate dielectric and the substrate in 43. Shah J, Brown R M Jr., "Towards electronic paper displays made from microbial cellulose", Appl Microbial Biotechnol 66, 352 (2005). DOI101007/s00253-004-1756-6.
44. Sawan M, Mountaim F, Lesbros G, "Wireless monitoring of electrode tissues interfaces for long term characterization," Analog Integrated circuits signal processing 55, 103 (2008).
45. Chen W M, Chiueh H, Chen T J, Ho C L, Jeng C, Ker M D, Lin C Y, Huang Y C, Chou C W, Fan T Y, Cheng M S, Hsin Y L, Liang S F, Wang Y L, Shaw F Z, Huang Y H, Yang C H, Wu C Y, "A fully integrated 8-channel closed loop neural prosthetic CMOS Soc for real-time epileptic seizure control," Solid-State Circuits, IEEE Journal of, 49, 232, (2014).
46. Moon J S, Seo H C, Son K A, Yang B, Wong D, Le D, McGuire C, "20 Mb/s Zero-power graphene-on-glass microwave envelope detectors for ubiquitous ultra-low-power wireless network," in press, 2014 IEEE IMS.
47. Tucker R S, Hinton K, "Energy consumption and energy density in optical and electronic signal processing," IEEE Photon. J. 3, 821 (2011).
48. Baker M and Sarpeshkar R, IEEE Trans. Biomedical Circuits and Systems 1, 28 (2007).
49. Ekanadham C., Tranchina D., Simoncelli E P. A blind deconvolution method for neural spike identification. Neural Information Processing Systems. 2011.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A method for fabricating a graphene-based neuroelectric sensor comprising:
   providing a bio-compatible microbial cellulose (MBC) membrane on a handling wafer;
   passivating the bio-compatible microbial cellulose (MBC membrane with an atomic layer deposition (ALD) of dielectric, or with a bio-compatible polymer;
   transferring graphene over the passivated bio-compatible microbial cellulose (MBC) membrane;
   patterning the transferred graphene;
   etching the patterned graphene to form a graphene mesa structure;
   forming ohmic contacts on the graphene mesa structure for source and drain electrodes; and
   releasing the bio-compatible microbial cellulose (MBC) membrane from the handling wafer.

2. The method of claim 1 further comprising etching to remove the ALD dielectric or the bio-compatible polymer from a background nonactive area.

3. The method of claim 1 further comprising:
   forming a gate electrode integrated with a gate dielectric.

4. The method of claim 1 further comprising:
   forming electrical contacts for a multiplexer and for an electrical ground.

5. The method of claim 1 wherein the handling wafer is Si or glass.

6. The method of claim 1 wherein etching the patterned graphene to form graphene mesa structures comprises oxygen plasma etching.

7. The method of claim 1 wherein forming ohmic contacts for source and drain electrodes comprises using a biocompatible Ti alloy.

8. The method of claim 3 wherein forming a gate electrode comprises using a biocompatible metal or a metal alloy.

9. The method of claim 4 wherein forming electrical contacts for a multiplexer and for an electrical ground comprises using a biocompatible metal or a metal alloy.

10. The method of claim 1 further comprising:
    passivating the source and drain electrodes with a biocompatible polymer.

11. The method of claim 3 further comprising:
    passivating the gate electrode with a biocompatible polymer.

12. The method of claim 4 further comprising:
    passivating the electrical contacts for the multiplexer and for the electrical ground with a biocompatible polymer.

13. The method of claim 1 wherein the graphene is grown by chemical vapor deposition.

* * * * *